United States Patent [19]

DeVor

[11] Patent Number: Plant 6,142

[45] Date of Patent: Apr. 5, 1988

[54] WHITE TEA ROSE NAMED LADY LIBERTY

[75] Inventor: Thomas R. DeVor, Orland, Calif.

[73] Assignee: Joseph H. Hill Company, Richmond, Ind.

[21] Appl. No.: 844,367

[22] Filed: Mar. 26, 1986

[51] Int. Cl.[4] ..... A01H 5/00
[52] U.S. Cl. ..... Plt./14
[58] Field of Search ..... Plt. 14

*Primary Examiner*—Robert E. Bagwill

*Attorney, Agent, or Firm*—Charles W. Rummler; John B. Lungmus

[57] ABSTRACT

A white tea rose cultivar intended for greenhouse culture and cut flower production, the new plant being distinguished by its continuous and profuse production of large, clear white flowers borne on long, strong and sturdy stems and having a very excellent vase life. In greenhouse culture, this plant has a free branching, upright and vigorous growth habit with an abundant production of foliage of medium size.

2 Drawing Sheets

BACKGROUND OF THE NEW PLANT

This new rose cultivar originated at Orland, Calif., as a sport of the variety "Lady Diana" (U.S. Plant Pat. No. 5,360) and was discovered by me in the summer of 1983. The size and clear white color of the flowers prompted me to reproduce this new plant by budding at Orland with very favorable results and subsequent propagation, also by budding, at Pleasanton, Calif., clearly demonstrated that the distinctive characteristics of this new plant would hold true from generation to generation and appeared to be firmly fixed.

DESCRIPTION OF THE DRAWINGS

My new variety of rose plant is illustrated by the accompanying full color photographic drawings which show a full face view of a newly opened flower in FIG. 1, a group of four stems illustrating the development of the blossom from newly opened bud to fully opened flower in FIG. 2, and in FIG. 3, specimens of wood, top and bottom views of leaves and a bud on which the sepals are just beginning to divide.

DESCRIPTION OF THE NEW PLANT

Figure 1:
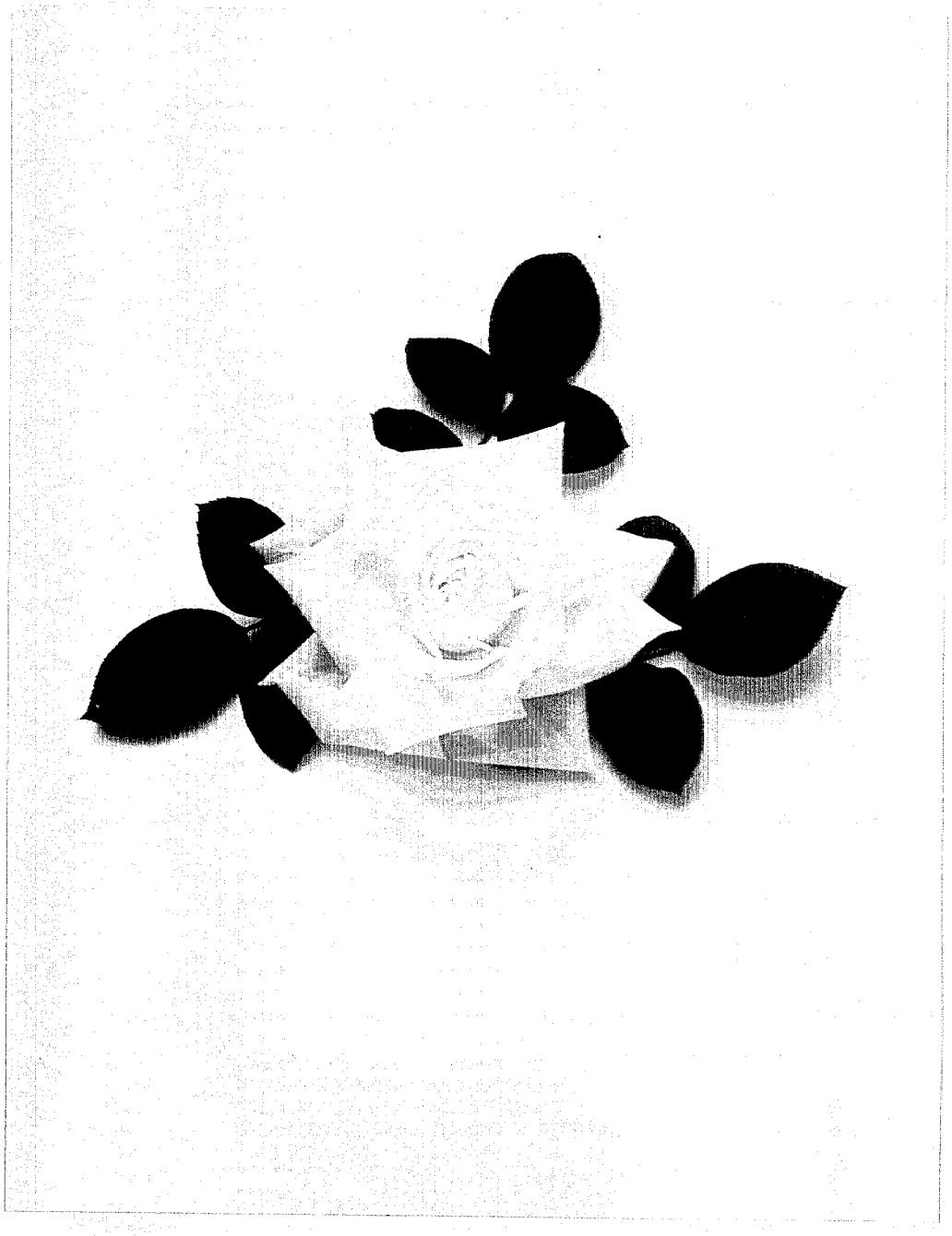
Figure 2:
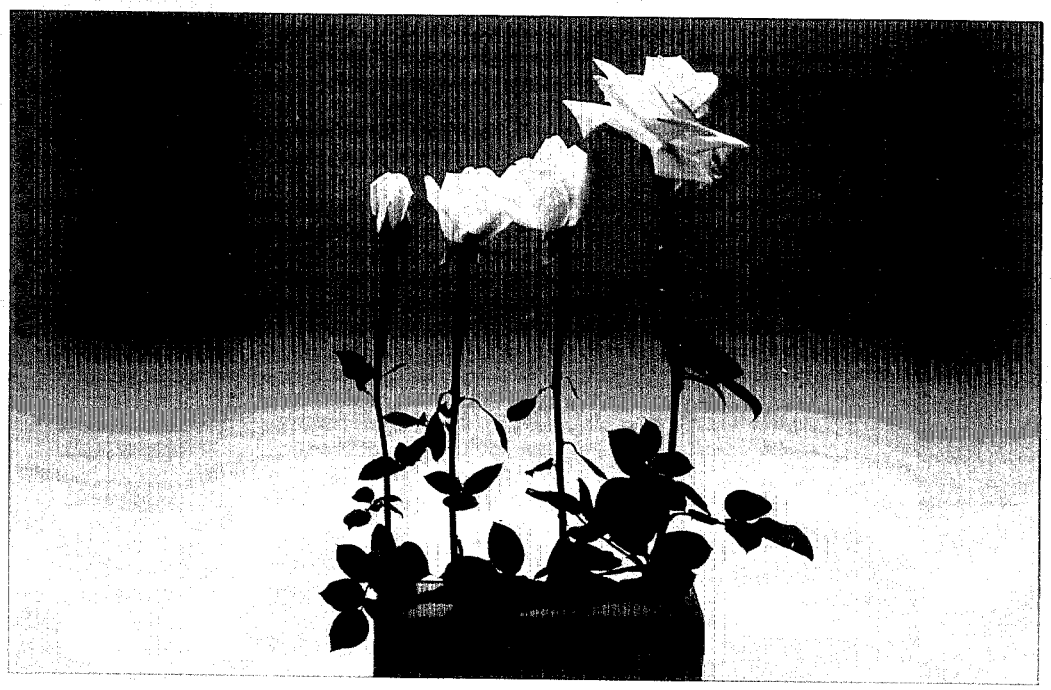
Figure 3:
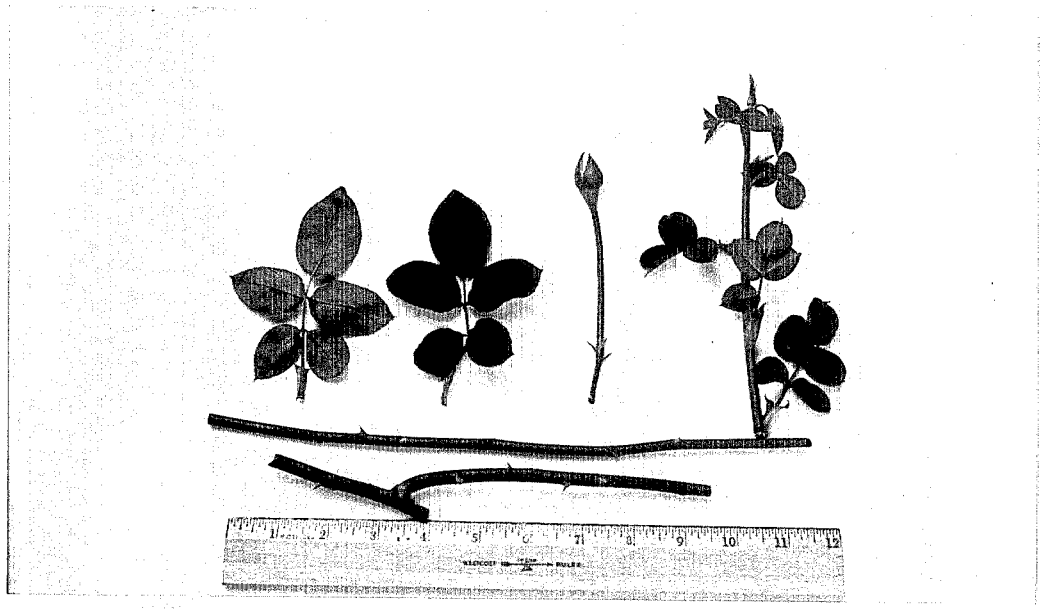

The following is a detailed description of my new variety of rose based upon observations of greenhouse plants grown at Orland, Calif., the color designations being made according to The R.H.S. Colour Chart published by The Royal Horticultural Society at London, England.

THE PLANT

Parentage: Sport of "Lady Diana", U.S. Plant Pat. No. 5,360.
Classification:
- *Botanic.*—Hybrid Tea.
- *Commercial.*—Greenhouse rose for cut flower production.

Form: Upright bush.
Height: 165 to 185 cm.
Growth: Vigorous, erect and free branching.
Main stems:
- *Length.*—About 120 cm.
- *Color.*—Yellow Green, 147B.

Thorns: Very sparse, dilated main stem of cut flowers having no thorns.

- *Color.*—Orange Red, 35B.
- *Size.*—About 6 mm. in length.

Foliage:
- *Quantity.*—Abundant.
- *Number of leaves.*—12 to 16 and spaced apart from about 6.2 to 9 cm. on flower stems.
- *Size of leaf.*—About 4.3 to 5.6 cm. in width.
- *Shape.*—Odd pinnate, in generally oval outline.

Leaflets:
- *Number.*—3 to 5.
- *Size.*—About 2.5 to 3.5 cm. in length.
- *Shape.*—Oval with serrated margins.
- *Texture.*—Smooth and medium leathery.
- *Color.*—Upper side — Yellow Green, 147A. Under side — Green, 138B.
- *Ribs and veins.*—Ribs prominent on both sides. Veins seen only on reverse side.

Rachis: About 4 cm. for five leaflets and 1.1 cm. for three leaflets.
Petiolule: About 1 mm. long.
Petioles: About 1.3 cm. long.
Stipules: About 2 cm. long, hairy and adnate.

THE BUD

Shape: Long and pointed.
Size: Large.
- *Diameter.*—About 7 to 8.8 cm.
- *Length.*—About 4.3 to 5.1 cm.

Opening rate: Very slowly.
Sepals:
- *Shape.*—Ovate acuminate.
- *Number.*—Five.
- *Character.*—Sepals curl back when flower opens.
- *Color.*—Inside — Yellow Green, 148D. Outside — Yellow Green, 144B.

Color of petals:
- *When sepals first divide.*—Red, 36D.
- *When petals begin to unfurl.*—White, 155B.

Calyx:
- *Shape.*—Funnel.
- *Size.*—Medium; about 1.2 cm. wide and about 1.5 cm. long.
- *Splitting.*—Calyx does not split.
- *Aspect.*—Smooth.

Peduncle:
- *Length.*—About 9 to 11 cm.
- *Character.*—Erect and rigid.

*Color.*—Green, 143C.

THE FLOWER

Blooming habit: Continuous and profusely the year around, blooming freely and in winter in greenhouse.

Size: Very large.

*Diameter.*—About 12.5 to 15 cm.

*Depth.*—About 5.5 to 6 cm.

Borne: Singly.

Shape:

*When bloom first opens.*—High centered.

*When bloom matures.*—Petals reflex.

Petalage:

*Number.*—35 to 37.

*Arrangement.*—Nicely imbricated.

*Texture.*—Velvety.

*Aspect.*—Smooth.

*Color.*—In general, White, 155B, the year around. Outer petal, White 155B. Base portion, Yellow, 4B. Reverse side, White 155C. Base portion, Yellow White, 158B. Inside petal: Body, White, 155A. Base, Yellow, 4A. Reverse side, White, 155A. Base, Yellow, 3A.

Petaloids:

*Number.*—Five.

*Size.*—About 1.9 to 4.5 cm.

*Color.*—White, 155D. Base, Yellow White, 158B.

Discoloration after full bloom: Holds color until flower drops.

Persistence: Petals hang on and dry.

Disease resistance: Moderately resistant to powdery mildew as observed at Pleasanton, Calif.

Lasting quality:

*On plant.*—14 to 20 days.

*As cut flower.*—12 to 14 days.

REPRODUCTIVE ORGANS

Stamens:

*Number.*—122 in slightly antrose arrangement.

Anthers:

*Size.*—2 mm.

*Color.*—Yellow Orange, 23C.

Filaments:

*Length.*—1.2 cm.

*Color.*—Yellow, 12D.

Pollen:

*Color.*—Yellow Orange, 23C.

Pistils:

*Number.*—68.

Styles:

*Length.*—1.6 cm.

*Color.*—White, 155D, tinged with Red, 41C.

Stigmas:

*Color.*—White, 155B.

Characteristics of ovaries: Dome shaped, covered with silvery thread-like hairs, styles unattached throughout.

This new rose variety most nearly resembles "Lady Diana", U.S. Plant Pat. No. 5,360, from which it sported and generally it is not considered to be better than "Lady Diana". It has the same good growth characteristics except that the flower is white.

The most distinctive feature about this white rose is the manner in which it excels in comparison to other white hybrid teas in flower form, stem length, greenhouse production and vase life, which makes it ideal for the flower market from grower to the end consumer.

I claim:

1. A new and distinct rose cultivar, substantially as herein shown and described, characterized by its profuse and continuous production of large flowers having clear white color throughout the body of each petal with the exception of a small amount of light yellow color at each petal base.

* * * * *